United States Patent
Chen et al.

(10) Patent No.: US 10,930,028 B2
(45) Date of Patent: Feb. 23, 2021

(54) IMAGING METHOD FOR COMPUTER TOMOGRAPHIC SYSTEM

(71) Applicant: DELTA ELECTRONICS, INC., Taoyuan (TW)

(72) Inventors: Sih-Yu Chen, Taoyuan (TW); Jhih-Shian Lee, Taoyuan (TW); Wen-Chieh Yang, Taoyuan (TW); Fang-Jing Li, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 438 days.

(21) Appl. No.: 15/870,900

(22) Filed: Jan. 13, 2018

(65) Prior Publication Data

US 2018/0211416 A1    Jul. 26, 2018

Related U.S. Application Data

(60) Provisional application No. 62/448,522, filed on Jan. 20, 2017.

(30) Foreign Application Priority Data

Oct. 31, 2017 (TW) ................. 10613755.1

(51) Int. Cl.
*G06T 11/00* (2006.01)
*A61B 6/03* (2006.01)
(Continued)

(52) U.S. Cl.
CPC ............ *G06T 11/003* (2013.01); *A61B 6/032* (2013.01); *A61B 6/4035* (2013.01); *A61B 6/488* (2013.01);
(Continued)

(58) Field of Classification Search
CPC ..................................... G06T 11/003
See application file for complete search history.

(56) References Cited

U.S. PATENT DOCUMENTS

| 7,695,193 B2* | 4/2010 | Flohr | ............... | A61K 49/04 378/207 |
| 8,000,510 B2* | 8/2011 | Boeing | ............ | A61B 6/482 382/128 |

(Continued)

FOREIGN PATENT DOCUMENTS

JP    2015523112 A    8/2015

OTHER PUBLICATIONS

Japanese Office Action issued in corresponding Japanese Application No. 2018-003572, dated Nov. 6, 2018, pp. 1-3.

*Primary Examiner* — David P Porta
*Assistant Examiner* — Djura Malevic
(74) *Attorney, Agent, or Firm* — Hauptman Ham, LLP

(57) ABSTRACT

An imaging method for computed tomographic system (1) includes following steps of: controlling a computed tomographic system (1) to receive a description operation for configuring description data; selecting one of a plurality of imaging parameter sets corresponding to different template data, wherein each imaging parameter set is used to maximize a contrast-to-noise ratio of the three-dimensional imaging data (34) matching with the corresponding template data; and, controlling the computed tomographic system (1) to execute a three-dimensional imaging operation according to the selected imaging parameter set for obtaining the three-dimensional imaging data (34). The present disclosed example has the ability of effectively reducing a technical threshold of operating the computed tomographic system (1) via automatically selecting the suitable one of the complex imaging parameter sets according to the comprehensible description operation.

12 Claims, 11 Drawing Sheets

(51) Int. Cl.
*A61B 6/00* (2006.01)
*H04N 5/32* (2006.01)

(52) U.S. Cl.
CPC ............ *A61B 6/508* (2013.01); *A61B 6/5211* (2013.01); *A61B 6/54* (2013.01); *A61B 6/544* (2013.01); *A61B 6/545* (2013.01); *G06T 2211/40* (2013.01); *H04N 5/32* (2013.01)

(56) References Cited

U.S. PATENT DOCUMENTS

| | | | | |
|---|---|---|---|---|
| 9,275,451 | B2* | 3/2016 | Ben-Haim | G06F 19/324 |
| 9,592,022 | B2* | 3/2017 | Larson | A61B 6/032 |
| 9,636,077 | B2* | 5/2017 | Braun | A61B 6/032 |
| 10,321,886 | B2* | 6/2019 | Choi | A61B 6/5264 |
| 2007/0076842 | A1* | 4/2007 | Tkaczyk | A61B 6/4085 |
| | | | | 378/5 |
| 2008/0310582 | A1* | 12/2008 | Flohr | A61B 6/488 |
| | | | | 378/5 |
| 2009/0043607 | A1* | 2/2009 | Nemoto | A61B 6/481 |
| | | | | 705/2 |
| 2010/0040268 | A1* | 2/2010 | Boeing | A61B 6/545 |
| | | | | 382/128 |
| 2010/0114597 | A1* | 5/2010 | Shreiber | G06F 19/321 |
| | | | | 705/2 |
| 2011/0200165 | A1* | 8/2011 | Pietsch | A61N 5/10 |
| | | | | 378/14 |
| 2011/0249797 | A1* | 10/2011 | Terunuma | A61N 5/1049 |
| | | | | 378/65 |
| 2012/0028211 | A1* | 2/2012 | Palti | A61C 9/0053 |
| | | | | 433/71 |
| 2014/0233820 | A1* | 8/2014 | Wu | A61B 6/5211 |
| | | | | 382/131 |
| 2014/0270052 | A1* | 9/2014 | Vestevich | A61B 6/501 |
| | | | | 378/4 |
| 2014/0270053 | A1* | 9/2014 | Larson | A61B 6/032 |
| | | | | 378/4 |
| 2015/0085971 | A1* | 3/2015 | Braun | A61B 6/544 |
| | | | | 378/8 |
| 2015/0103971 | A1* | 4/2015 | Chen | A61B 6/482 |
| | | | | 378/5 |
| 2015/0141813 | A1* | 5/2015 | Kalafut | A61B 6/545 |
| | | | | 600/425 |
| 2017/0209111 | A1* | 7/2017 | Choi | A61B 6/501 |

* cited by examiner

IMAGING METHOD FOR COMPUTER TOMOGRAPHIC SYSTEM

BACKGROUND OF THE INVENTION

Field of the Invention

The technical field relates to a computed tomography system, and more particularly related to an imaging method for a computed tomographic system.

Description of Related Art

At present, the computed tomography (CT) system has been widely used in medicine. An analyst (such as a physician or researcher) may obtain three-dimensional X-ray imaging data of a targeted object (such as a patient or an experimental mouse), and it helps to get the correct pathological analysis.

However, in an imaging method of the related art, the operator (such as a medical radiologist) must rely on the experience to set the imaging parameters (such as the X-ray tube voltage, the filters, or the projection number) of the computed tomography system one by one according to the requirement (such as type, size or application of a targeted object), such that the computed tomography system may execute the imaging operation correctly.

Above configuration of the imaging parameters is complex, so the operator may need to understand the best set of the imaging parameters for the different targeted objects after years of professional training or many attempts. This high technology threshold increases the operational difficulty of the computerized tomography system dramatically, and makes the computer tomography system fail to be used widely.

SUMMARY OF THE INVENTION

The present disclosed example is directed to an imaging method for a computed tomographic system, and the present disclosed example has the ability of selecting the best of the imaging parameter set according to the description of the targeted object.

One of the exemplary embodiments, an imaging method for a computed tomographic system comprises: controlling a computed tomographic system to receive a description operation for configuring description data under an intelligent imaging mode; selecting one of a plurality of imaging parameter sets corresponding to one of a plurality of different template data, wherein the template data corresponding to the selected imaging parameter set is consistent with the description data, each of the imaging parameter sets is used to maximize a contrast-to-noise ratio of the three-dimensional imaging data being consistent with the corresponding template data, each of the imaging parameter sets comprises at least two among of a X-ray tube voltage, a filter parameter, and a projection number of the description data; and controlling a X-ray tube, a filter module or an image detector of the computed tomographic system to execute a three-dimensional imaging operation according to the selected imaging parameter set for obtaining the three-dimensional imaging data being consistent with the description data.

The present disclosed example has the ability of effectively reducing a technical threshold of operating the computed tomographic system via automatically selecting the suitable one of the complex imaging parameter sets according to the comprehensible description operation.

BRIEF DESCRIPTION OF DRAWING

The features of the present disclosed example believed to be novel are set forth with particularity in the appended claims. The present disclosed example itself, however, may be best understood by reference to the following detailed description of the present disclosed example, which describes an exemplary embodiment of the present disclosed example, taken in conjunction with the accompanying drawings, in which:

DETAILED DESCRIPTION OF THE INVENTION

In cooperation with attached drawings, the technical contents and detailed description of the present disclosed example are described thereinafter according to a preferable embodiment, being not used to limit its executing scope. Any equivalent variation and modification made according to appended claims is all covered by the claims claimed by the present disclosed example.

Figure 1A:
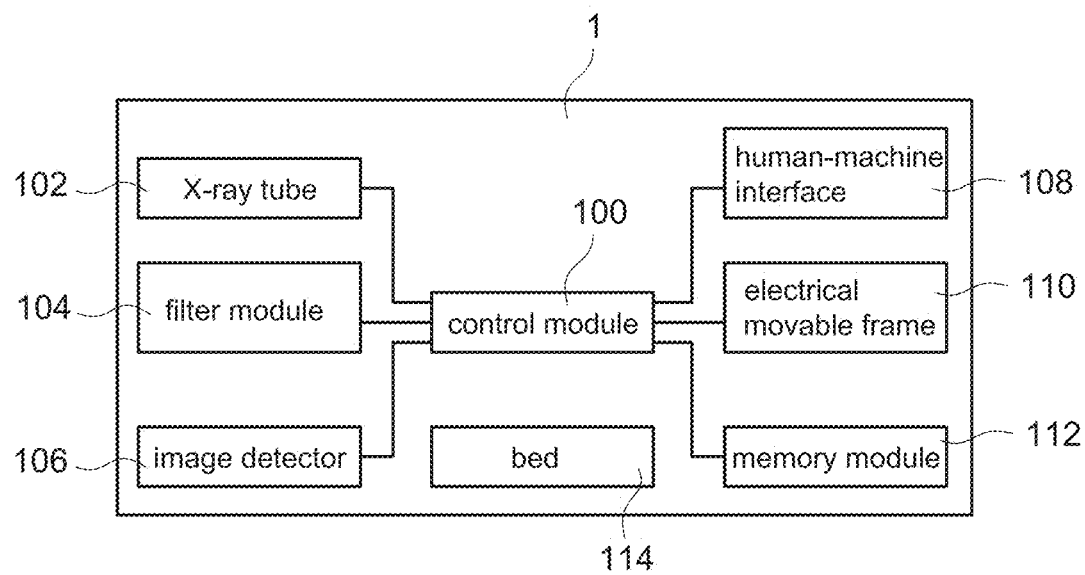
FIG. 1A is an architecture diagram of a computed tomography system according to the first embodiment of the present disclosed example.

First, please refer to FIG. 1A, which is an architecture diagram of a computed tomography system according to the first embodiment of the present disclosed example. As shown in figure, this embodiment discloses a computed tomography system 1. The computed tomography 1 comprises a control module 100, an X-ray tube 102, a filter module 104, an image detector 106, a human-machine interface 108, an electrical movable frame 110, a memory module 112 and a bed 114.

The control module 100 is electrically connected to the X-ray tube 102, the filter module 104, the image detector 106, the human-machine interface 108, the electrical movable frame 110, and the memory module 112. The control module 100 is configured to control the operation of the computed tomography system 1.

The X-ray tube 102 is configured to convert electrical energy into X-rays and emit the X-rays. The filter module 104 is arranged in a light path of above X-rays, and has the ability of adjusting a penetrability of the X-rays via controlling a plurality of filter mirrors to adjust energy intensity of the X-rays. The image detector 106 is arranged in the light path of above X-rays, and is configured to receive the X-rays penetrating the targeted object (such as the targeted object 2 shown in FIG. 1B). The image detector 106 comprises a plurality of sensor dots configured to sense the flux of the X-rays. The computed tomography system 1 may calculate each total flux of the X-rays received by each of the sensor dots, and generate a two-dimensional imaging image (two-dimensional X-ray image) according to each total flux. The human-machine interface 108 (such as buttons, a mouse, a touch-pad or the other input device, indicators, a printer, a speaker, a display or the other output device, or any combination of above devices) is configured to receive a user operation and display the related information. The bed 114 is configured to carry the targeted object (such as a patient or a rat for experiment) being imaged.

The electrical movable frame 110 is configured to arrange the X-ray tube 102, the filter module 104 and the image detector 106. The electrical movable frame 110 may be configured to move around the bed 114, and make the X-ray tube 102, the filter module 104 and the image detector 106 execute an imaging operation at different angular projections of the bed 114. The memory module 112 is configured to store data (such as an imaging parameter set described later).

Figure 1B:
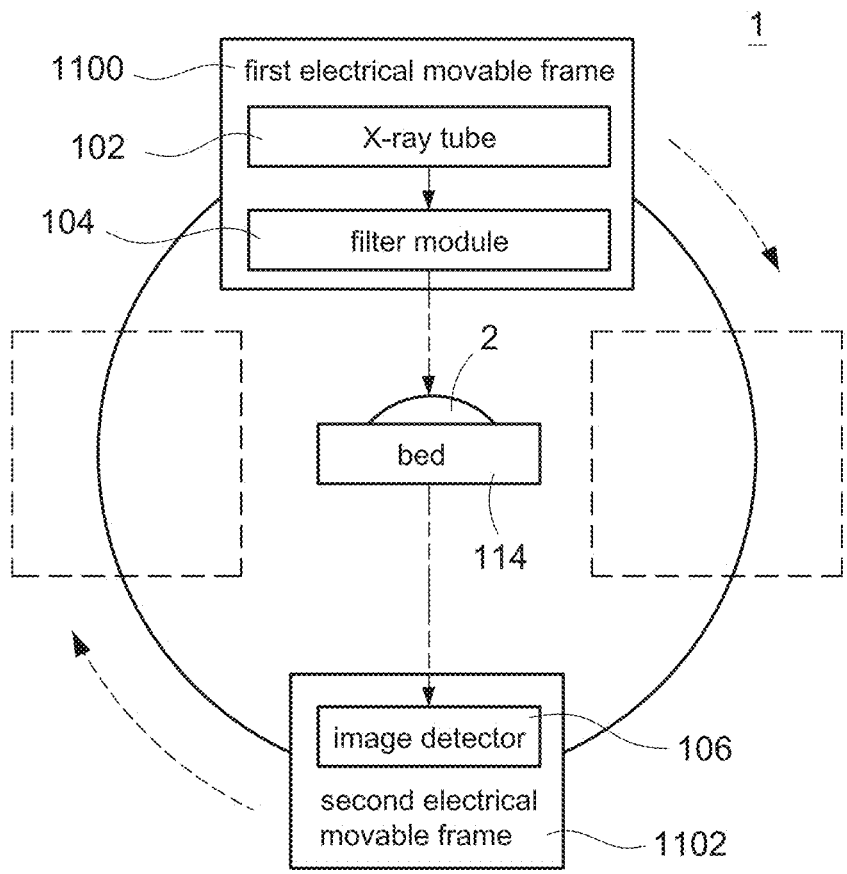
FIG. 1B is an imaging schematic view of a computed tomography system according to the first embodiment of the present disclosed example.

Please refer to FIG. 1B, which is an imaging schematic view of a computed tomography system according to the first embodiment of the present disclosed example. As shown in the figure, the electrical movable frame 110 further comprises a first electrical movable frame 1100 and a second electrical movable frame 1102 arranged at the both sides of the bed 114 respectively. The first electrical movable frame 1100 is configured to arrange the X-ray tube 102 and the filter module 104. The second electrical movable frame 1102 is configured to arrange the image detector 106. Moreover, the second electrical movable frame 1102 may move around the carrier bed 114 relative to the first electrical movable frame 1100 when the first electrical movable frame 1100 moves around the carrier bed 114. Thus, the first electrical movable frame 1100 and the second electrical movable frame 1102 may be kept on both sides of the bed 114 always.

Following description is used to explain how to execute a three-dimensional imaging operation. First, the control module 100 controls the first electrical movable frame 1100 and the second electrical movable frame 1102 move around the bed 114. Then, the control module 100 controls the computed tomography system 1 to execute a two-dimensional imaging operation for obtaining a two-dimensional X-ray image of the targeted object 2 corresponding to the different perspective when rotating around the bed 114 for a specific angle (the specific angle relates to the projection number) every time.

Please note that the above-mentioned two-dimensional imaging operation is to control the X-ray tube 102 and the filter module 104 arranged on the first electrical movable frame 1100 to emit the X-rays having the specific energy level, and the X-rays is received by the image detector 106 arranged on the second electrical movable frame 1102 after penetrating the targeted object 2.

Then, the control module 100 controls the first electrical movable frame 1100 and the second electrical movable frame 1102 move a default distance heading a direction being vertical with the detour track, and execute above-mentioned two-dimensional imaging operation again, and so on. Thus, the computed tomography system 1 can obtain a plurality of two-dimensional X-ray images respectively corresponding to different angular projections, and generate a set of three-dimensional imaging data according to the two-dimensional X-ray images.

Figure 2:
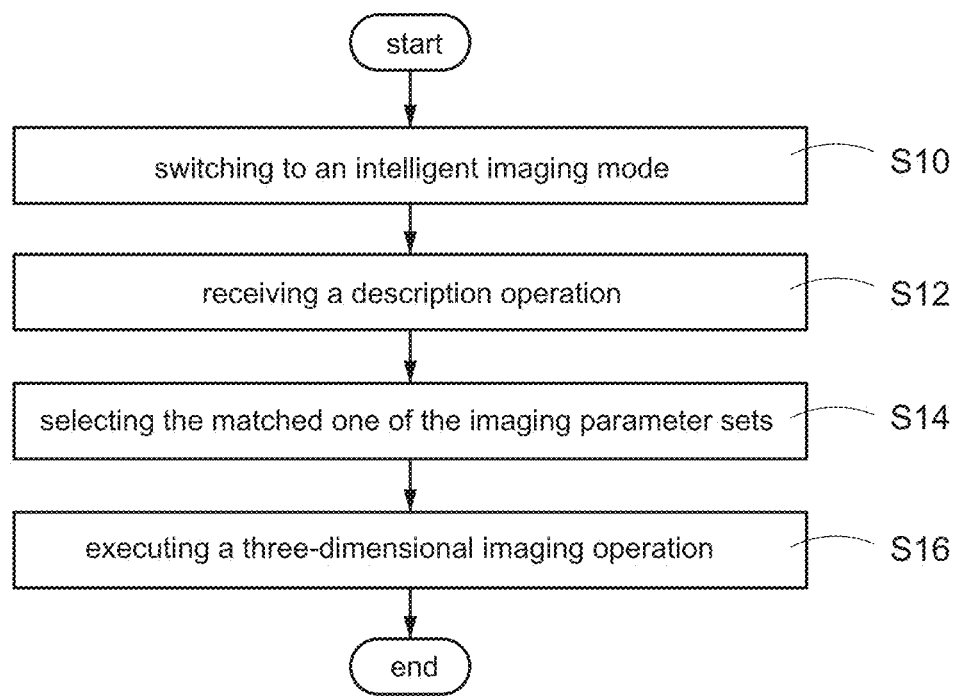
FIG. 2 is a flowchart of an imaging method according to the first embodiment of the present disclosed example.

Please refer to FIG. 2, which is a flowchart of an imaging method according to the first embodiment of the present disclosed example. The imaging method of each embodiment of the present disclosed example can be implemented by any of the computed tomography system 1 shown in FIG. 1A and FIG. 1B. In this embodiment, the present disclosed example provides an intelligent imaging function. Via implement of the intelligent imaging function, the present disclosed example may generate complex imaging parameter set used to control the computed tomography system 1 according to the description operation after the user only has necessary to input a comprehensible description operation according to this requirement of the three-dimensional imaging.

In this embodiment shown in FIG. 2, the memory module 112 of the computed tomography system 1 further stores a computer software, and the computer software records a plurality of computer readable codes. The control module 100 may control the computed tomography system 1 to perform the following steps S10-S16 after execution of the computer software.

Step S10: the control module 100 switches to an intelligent imaging mode. More specifically, the control module 100 switches to the intelligent imaging mode automatically after a default condition satisfies.

Step S12: the control module 100 receives the description operation by the human-machine interface 108 from the user, and configures the corresponding description data according to the received description operation.

In one of the exemplary embodiments, the above-mentioned description operation is for describing this three-dimensional imaging requirement based on the comprehensible natural language. For example, the description operation may be a selection of type and size of the targeted object (such as rat, mouse, large dog, small dog or isolated tissue) and/or a selection of applications for imaging (such as bone, muscle, metal, lung or abdomen). Moreover, the control module 100 may transfer the above-mentioned description operation into the description data which can be analyzed by the computer. In one of the exemplary embodiments, the description data may comprise one or more variables (such as input body type or input application), and the control module 100 configures the value of each variable of the description data according to the description operation.

Take the description data comprising the input body type for example, the computed tomography system 1 may be configured to provide five body type options (such as a rat, mouse, large dog, small dog or isolated tissue), and the five body type options correspond to five variable values (such as 0, 1, 2, 3 and 4) respectively. The control module 100 configures the value of the input body type to be 0 (namely, configuring type=0) after the user selects the body type option of a rat, and configures the value of the input body type to be 1 (namely, configuring type=1) after the user selects the body type option of a mouse, and so on.

Step S14: the control module 100 selects one of imaging parameter sets matched the current description data from a plurality of the imaging parameter sets.

More specifically, the memory module 11 is configured to store a plurality of the imaging parameter sets in advance, and the imaging parameter sets correspond to a plurality of template data configured in advance. In one of the exemplary embodiments, each template data may comprise one or more variables which is/are the same as the variable(s) of the description data. Moreover, the values of the variables are different with each other.

In the step S14, the control module 100 may further compare the description data configured in the step S12 with each template data for determining whether the description data matches any of the plurality of the template data.

In one of the exemplary embodiments, the control module 100 may compare all of the values of the variables of the description data with all of the values of the variables of each template data one by one, and determine that the description data matches with the template data if all of the values of the variables of any template data match with all of the values of the variables of the description data.

In the step S14, the control module 100 may further select the matched template data and load the imaging parameter set corresponding to this template data after determining that the description data matches with one of the plurality of the template data.

In one of the exemplary embodiments, each of the above-mentioned imaging parameter sets is used to maximize a contrast-to-noise ratio of the three-dimensional imaging data matching with each corresponding template data.

More specifically, the present disclosed example assumes various three-dimensional imaging requirements (such as a bone of rat, lung of rat, muscle of small dog, lung of small dog and so on) in advance, experiments and analyzes based on each of the assumed three-dimensional imaging requirements for obtaining each of best imaging parameter sets respectively being suitable for each of three-dimensional imaging requirements, and makes the best imaging parameter sets correspond to the template data used to described the three-dimensional imaging requirement.

Take providing three template data of first template data, second template data and third template data, (namely, providing three three-dimensional imaging requirements) for example, the first template data is {rat, bone}, the second template data is {mouse, muscle}, and the third template data is {mouse, abdomen}. The analysts may operate the computed tomography system 1 to execute the three-dimensional imaging operations respectively based on the various imaging parameter sets on the bone of rat for obtaining a plurality of three-dimensional imaging data matching with the first template data, select one of the plurality of the three-dimensional imaging data (such as selecting the three-dimensional imaging data having the best contrast), the contrast of each three-dimensional imaging data may be calculated by a formula 1 to formula 3 described later), and configure the imaging parameter set user to generate the selected three-dimensional imaging data to correspond to the first template data, and so on. Thus, the present disclosed example can establish association between the comprehensible template data the complex imaging parameter set.

Please note that the computed tomography system 1 may generate the three-dimensional imaging data having the maximum contrast-to-noise ratio (namely, the different physiological tissues can be distinguished from the three-dimensional imaging data) after execution of the three-dimensional imaging operation based on the imaging parameter set corresponding to this template data when the current description data matches with any of the plurality of the template data.

In one of the exemplary embodiments, each imaging parameter set comprises a combination of various imaging parameters for execution of the three-dimensional imaging operation, such as X-ray tube voltage, filter parameter, and/or projection number.

In one of the exemplary embodiments, the control module 100 first loads each of the plurality of template data from the memory module 112, rather that each of the imaging parameter sets. After the most matched template data is determined, the control module 100 loads the imaging parameter set corresponding the most matched template data for the memory module 112. Thus, the present disclosed example can effectively reduce the loaded data volume and enhance the process performance because of only one imaging parameter set having necessary to load.

Step S16: the control module 100 controls the computed tomography system 1 to execute the three-dimensional imaging operation based on the selected imaging parameter set for obtaining the three-dimensional imaging data matched with the description data.

Take the imaging parameter set comprising X-ray tube voltage, filter parameter, and projection number for example, the control module 100 controls the X-ray tube 102 to adjust the energy intensity of X-rays according to the X-ray tube voltage, controls the filter module 104 to adjust energy spectrum of the X-rays according to the filter parameter, and controls the electrical movable frame 110 and the image detector 106 to adjust the number of the two-dimensional X-ray images according to the projection number.

Thus, the present disclosed example can configure the most suitable imaging parameter set according to the description data selected by the user, and achieves the best imaging effect, such as the imaging range, the imaging resolution, the focal spot size, the pixel binning, the penetration of the X-rays, and so on of the generated three-dimensional imaging data match the current description.

The present disclosed example has the ability of effectively reducing a technical threshold of operating the computed tomographic system via automatically selecting the suitable one of the complex imaging parameter sets according to the comprehensible description operation.

Figure 3:
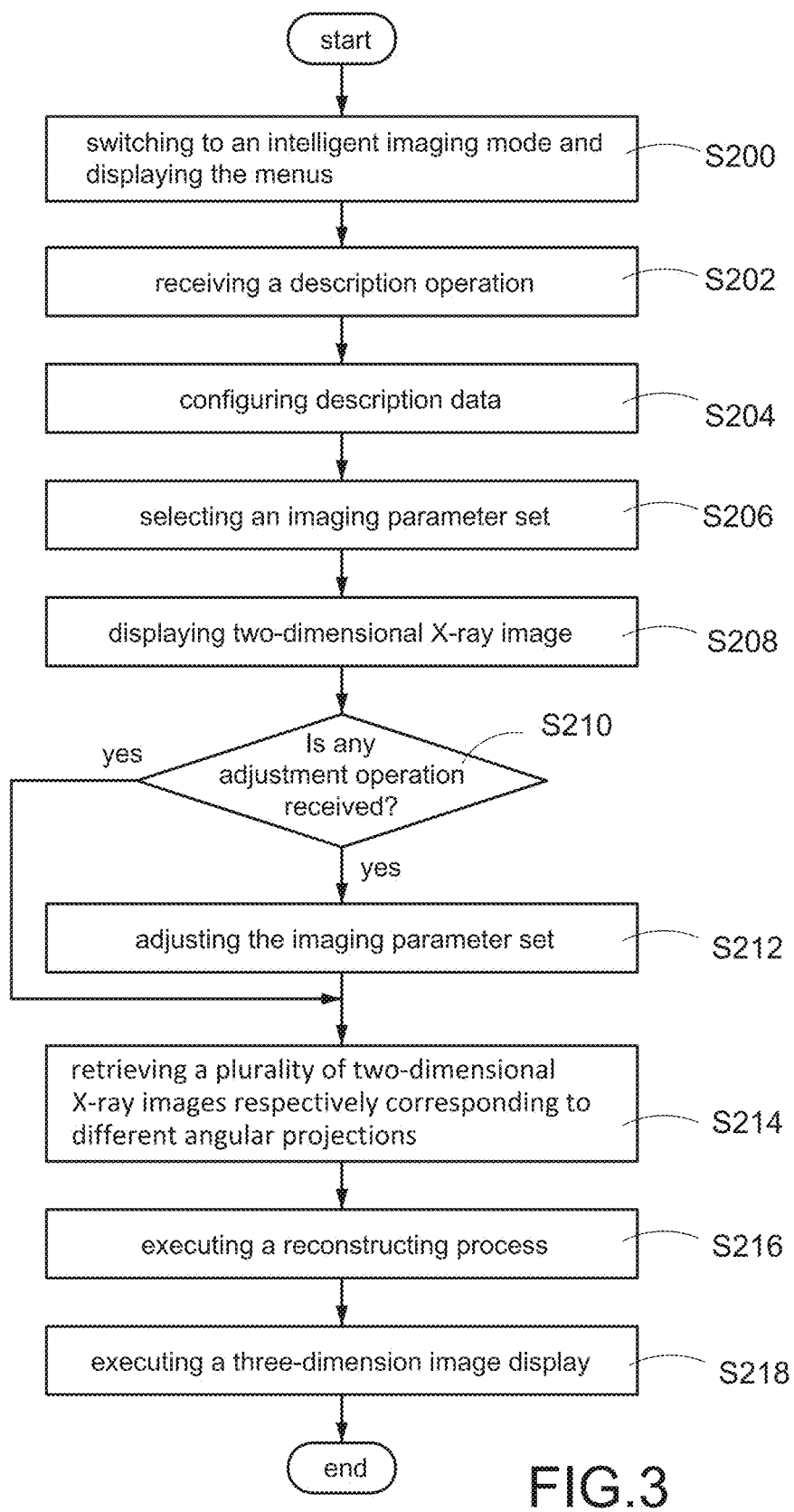
FIG. 3 is a flowchart of an imaging method according to the second embodiment of the present disclosed example.
Figure 10:
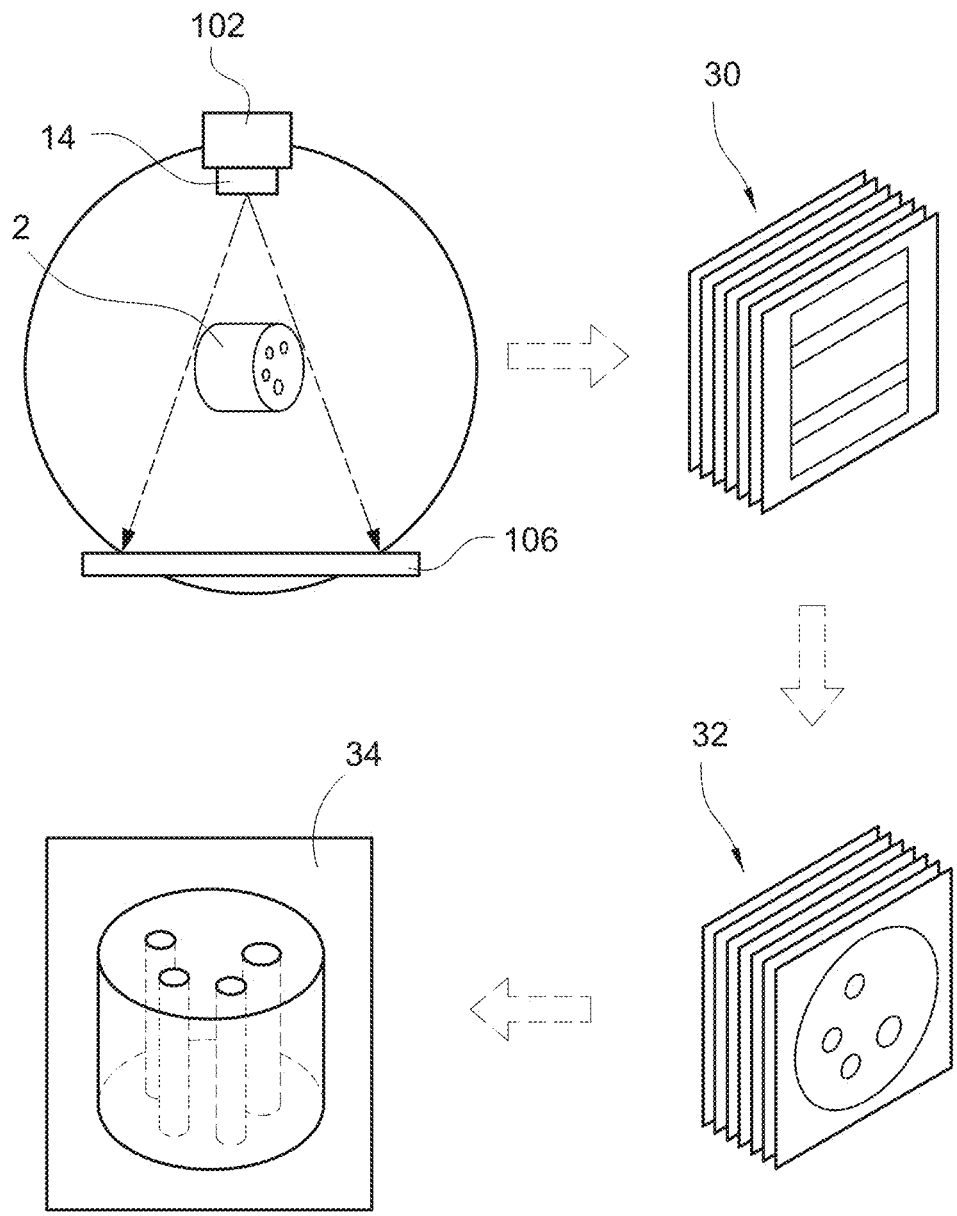
FIG. 10 is a schematic view of a three-dimensional imaging operation according to one embodiment of the present disclosed example.
Figure 11:
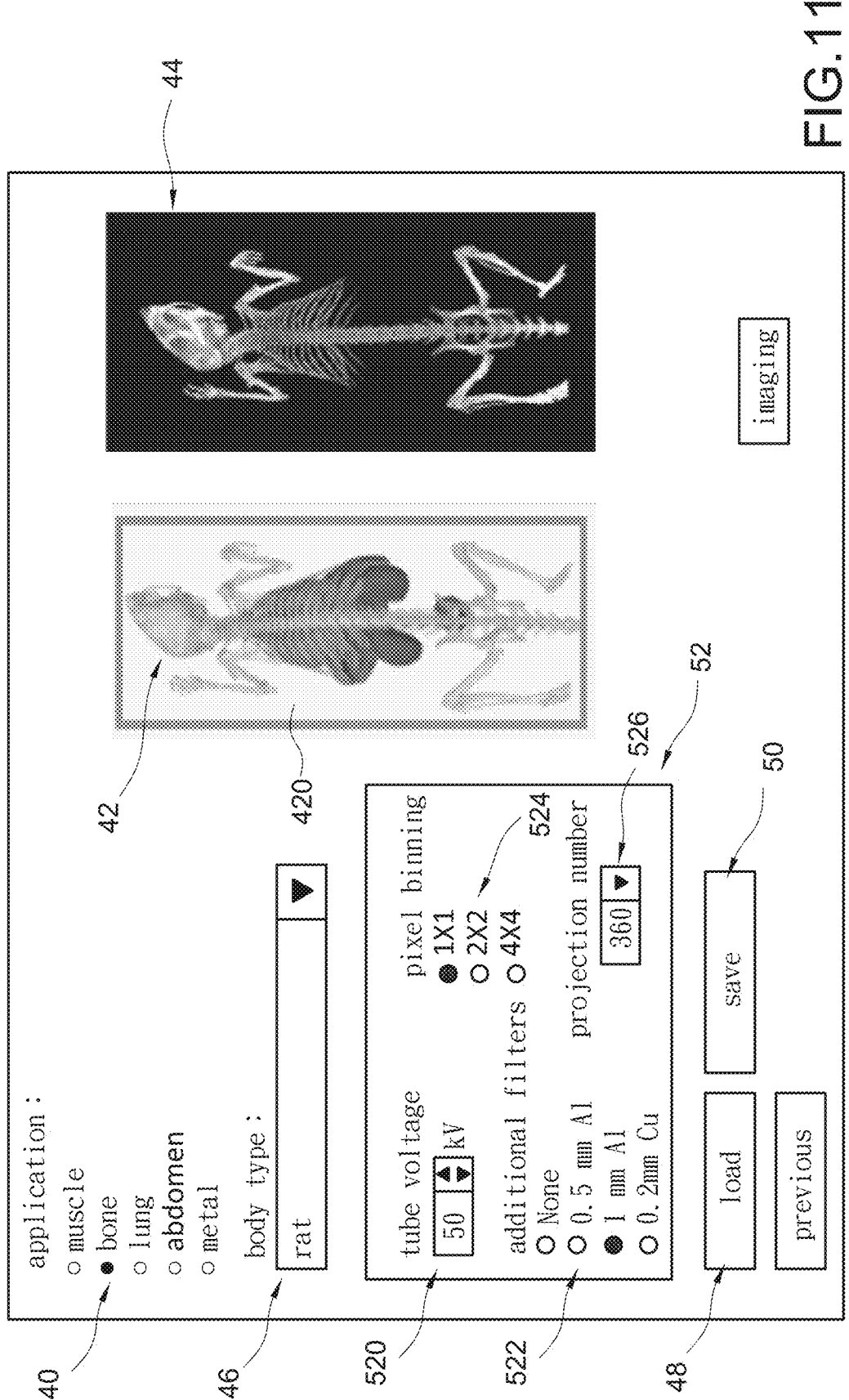
FIG. 11 is a first schematic view of operation interface according to one embodiment of the present disclosed example.
Figure 12:
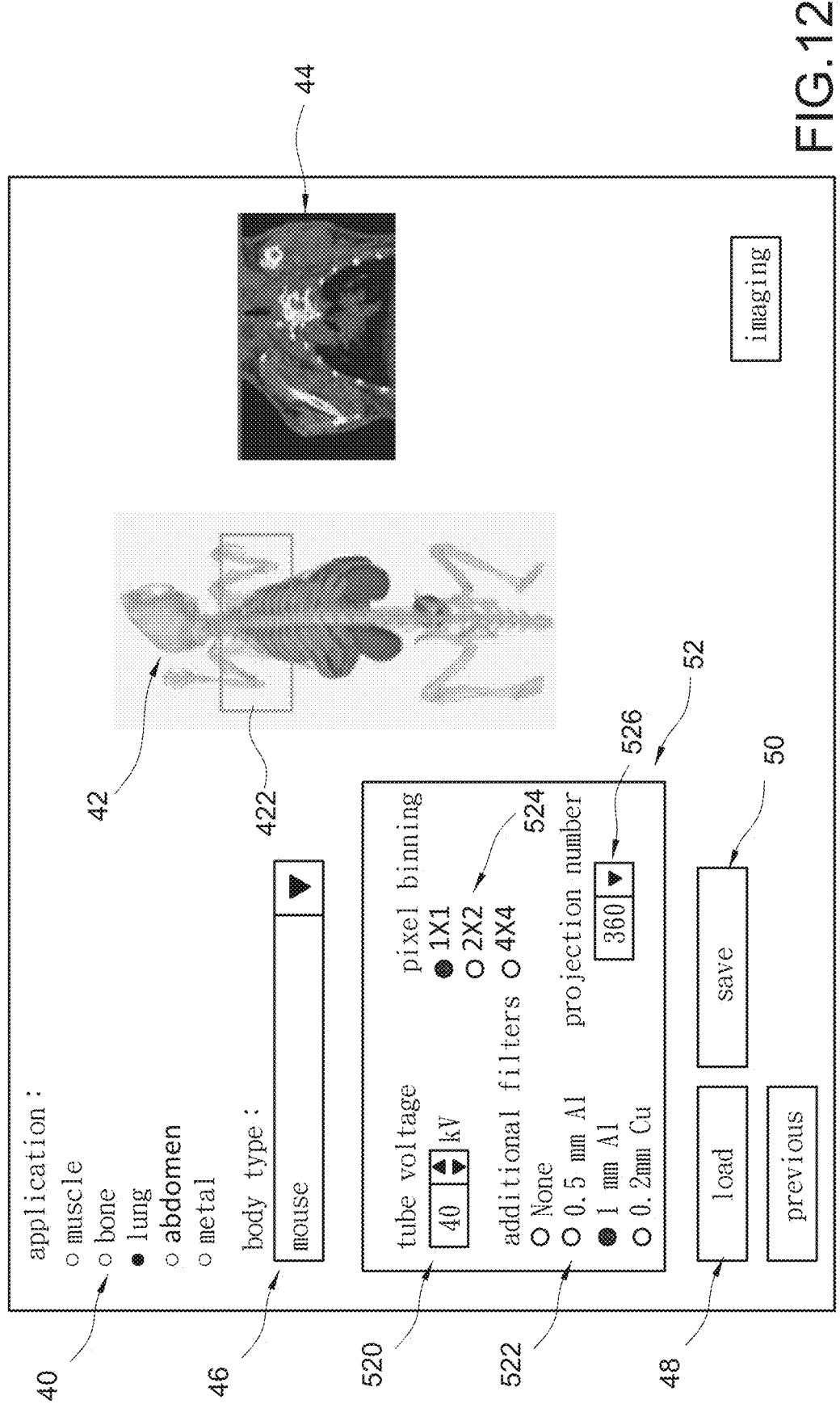
FIG. 12 is a second schematic view of operation interface according to one embodiment of the present disclosed example.

Please refer to FIG. 3, FIG. 10, FIG. 11 and FIG. 12 together, FIG. 3 is a flowchart of an imaging method according to the second embodiment of the present disclosed example, FIG. 10 is a schematic view of a three-dimensional imaging operation according to one embodiment of the present disclosed example, FIG. 11 is a first schematic view of operation interface according to one embodiment of the present disclosed example, and FIG. 12 is a second schematic view of operation interface according to one embodiment of the present disclosed example.

The present disclosed example further implements a visualization selection function having the ability of making the user input the description more intuitively. More specifically, in this embodiment, the human-machine interface 108 comprises a display, the control module 100 controls the display to display a graphical user interface (GUI) (as the operation interface shown in FIG. 11 and FIG. 12), and receives the description operation from the user via the GUI. Moreover, in this embodiment, the description data inputted by the user comprises an input body type and an input application. Each template data comprises a template body type and a template application. The imaging method of this embodiment comprises following steps.

Step S200: the control module 100 switches to an intelligent imaging mode, and controls the display to display one or more menu after switching to the intelligent imaging mode. Each menu comprises a plurality of options respectively corresponding to the difference description data. Thus, the user can achieve the purpose of configuring the different description data via selecting the different options in each menu.

For example, the control module 100 may control the display to display an application menu 40 (taking checkbox menu for example in FIG. 11 and FIG. 12), the above-mentioned application menu 40 comprises a plurality of application options which are "muscle", "bone", "lung", "abdomen", and "metal".

In addition, the control module 100 may further control the display to display a body type menu 46 (taking drop-down menu for example in FIG. 11 and FIG. 12), the above-mentioned body type menu 46 comprises a plurality of body type options which are "rat" and "mouse".

Step S202: the control module 100 receives the description operation from the user via the human-machine interface 108 and the GUI.

For example, the human-machine interface 108 comprises input device, such as keyboard, mouse, or touchpad. The user may operate the input device to select the application option "bone" (as shown in FIG. 11) or the application option "lung" (as shown in FIG. 12) in the application menu 40. Moreover, the user may operate the input device to select the body type option "rat" (as shown in FIG. 11) or the body type option "mouse" (as shown in FIG. 12) in the body type menu 46.

Step S204: the control module 100 configures the input application and the input body type of the description data according to the selected application option and the selected body type option. More specifically, the control module 100 configures the application option selected by the user as the input application of the description data, and configures the body type option selected by the user as the input body type of the description data. Thus, the present disclosed example can configure the corresponding description data according to the user's description operation.

Step S206: the control module 100 selects one of the imaging parameter sets, and the selected imaging parameter set is most suitable to the current description data. More specifically, the control module 100 first recognizes and selects one of a plurality of template data, the template body type of the selected template data matches with the input body type, and the template application of the selected template data matches with the input application. Then, the control module 100 selects the imaging parameter set corresponding to the selected template data.

Step S208: the control module 100 controls the display to display a two-dimensional X-ray image. Moreover, above-mentioned two-dimensional X-ray image corresponds to the application option (namely, the input application) selected by the user and/or the body type option (namely, the input body type) selected by the user.

In one of the exemplary embodiments, the above-mentioned two-dimensional X-ray image is a pre-stored two-dimensional X-ray image. More specifically, the memory module 112 may store a plurality of pre-stored two-dimensional X-ray images in advance, each of the pre-stored two-dimensional X-ray images corresponds to one template data, such as corresponding to one template body type (such as "rat"), one template application (such as "bone"), or a combination of template application and template body type (such as {rat, bone}). The control module 100 may control the display to display the pre-stored two-dimensional X-ray image 44 (the two-dimensional X-ray image 44 shown in FIG. 11 corresponding to {rat, bone}, the two-dimensional X-ray image 44 shown in FIG. 12 corresponding to {mouse, lung}) corresponding to the matched template data according to the description data inputted by the user.

In one of the exemplary embodiments, the above-mentioned two-dimensional X-ray image is a pre-scanned two-dimensional X-ray image. More specifically, the control module 100 may control the computed tomography system 1 to execute two-dimensional imaging operation for obtaining a tested two-dimensional X-ray image according to the selected imaging parameter set, and control the display to display the tested two-dimensional X-ray image.

In one of the exemplary embodiments, the control module 100 may further control the display to display an atlas of anatomy for assisting the user to determine whether the current inputted three-dimensional imaging requirement (and the inputted description data) is correct. For example, the memory module 112 may store a plurality of atlases of anatomies respectively corresponding to the various body type options and/or various application options in advance. The control module 100 may control the display to display the corresponding atlas of anatomy (an atlas of anatomy 42 of rat is shown in FIG. 11, an atlas of anatomy 42 of mouse is shown in FIG. 12) according to the selected body type option and/or application option.

In one of the exemplary embodiments, the control module 100 may further control the display to display a mark on an imaging range corresponding to the selected application option in the atlas of anatomy 42 (the imaging range shown in FIG. 11 is whole body, and the imaging range shown in FIG. 12 is lung).

The present disclosed example can effectively reduce the difficulty of operation via making the user input the description data in a way of selection via GUI (namely, above-mentioned graphical menu), and improve the user experience.

Via display of the corresponding atlas of anatomy, pre-stored two-dimensional X-ray image, pre-scanned two-dimensional X-ray image and/or imaging range, the present disclosed example can assist the user to know clearly whether the configured description data can be used to generate an expected imaging image even the user is unfamiliar with the anatomic locations or imaging configuration, and can be easily determine whether the current description data is correct.

Although the user may directly select the input application and the input body type via menu in above-mentioned embodiment of the present disclosed example, but this specific example is not intended to limit the scope of the present disclosed example.

In the other embodiment, the present disclosed example arranges each option to be a complete schematic image of anatomical locations for selection by the user according to a physiological position of each corresponding input application.

More specifically, in the step S200, this embodiment is configured to display above-mentioned schematic image of anatomical locations, rather that application menu 40. Moreover, in the step S202, the user may operate the input device to press and select directly the input application (such as selecting directly "bone" or "lung") which the user wants to image on the schematic image of anatomical locations.

The imaging method of this embodiment further comprises steps S210-S212 for implementing a function of fine-tuning imaging parameters.

Step S210: the control module 100 controls the display to display a parameter adjustment interface 52, and determines whether any adjustment operation is inputted by the user via the parameter adjustment interface 52.

More specifically, the parameter adjustment interface 52 comprises a plurality of imaging parameter menu (such as tube voltage menu 520, filter menu 522, pixel binning menu 524 and projection number menu 526), and the control module 100 controls the display to display a plurality of parameter values of the current selected imaging parameter set. Moreover, the user may input the adjustment operation by the input device for adjusting at least one of a plurality of the parameter values of the current displayed imaging parameter set, such as adjusting the tube voltage from 40 kV to 50 kV.

If any adjustment operation is detected by the control module 100, the control module 100 performs step S212. Otherwise, the control module 100 performs step S214.

In the other embodiment, the present disclosed example further provides a function of storing imaging parameter set. More specifically, the control module 100 may control the display to display a loading button 48 and a saving button 50. After input of the adjustment operation, the user may further press the saving button 50. Thus, the control module 100 can store the adjusted imaging parameter set in the memory module 112.

Moreover, before execution of three-dimensional imaging operation corresponding to the same three-dimensional imaging requirement, the user may press the loading button 48. Then, the control module 100 may control the display to load the adjusted imaging parameter set from the memory module 112, and the description operation and the adjustment operation are omitted.

This embodiment can provide the user a more intuitive way of selection, and effectively improve the user experience.

After determination of imaging parameter set, the control module 100 may execute step S214-S218 to execute the three-dimensional imaging operation.

Step S214: the control module 100 controls the X-ray tube 102, the filter module 104, the image detector 106 and the electrical movable frame 110 to execute the two-dimensional imaging operation on the different angular projections of the targeted object for retrieving a plurality of two-dimensional X-ray images respectively corresponding to different angular projections according to the imaging parameter set.

In one of the exemplary embodiments, the imaging parameter set comprises X-ray tube voltage, filter parameter, projection number and/or effective focal spot of the X-ray tube 102. The control module 100 calculates the corresponding X-ray tube current according to the X-ray tube voltage and a default power value (may be stored in the memory module 112 in advance), detects a photon flux (sum of all pixel values) of the image detector 106 according to above conditions, and calculates the required exposure time for making the image detector 106 achieve the best performance.

In one of the exemplary embodiments, each imaging parameter set comprises at least two of the x-ray tube voltage, the X-ray tube voltage, the filter parameter, the projection number, and the effective focal spot of the X-ray tube 102.

Then, the control module 100 controls the X-ray tube 102 to emit the X-rays according to the X-ray tube voltage, X-ray tube current, and the effective focal spot, controls the filter module 104 to adjust X-ray energy spectrum (namely, adjustment of photon flux) according to the filter parameter, controls a movement angle of the electrical movable frame 110 moving each time according to the projection number, and controls the image detector 106 to obtaining the two-dimensional X-ray image according to the exposure time. Thus, the control module 100 can obtaining the two-dimensional X-ray images of the different angular projections of the targeted object, as the two-dimensional X-ray images 30 of the different angular projections shown in FIG. 10.

Step S216: the control module 100 executes a reconstructing process on the plurality of the two-dimensional X-ray images of the different angular projections for obtaining a plurality of difference slice images (such as the slice images 32 shown in FIG. 10).

Step S218: the control module 100 executes a three-dimension image display on the plurality of the slice images for obtaining the three-dimensional imaging data (such as the three-dimensional imaging data 34 shown in FIG. 10).

Please note that above-mentioned two-dimensional X-ray images 30 is a plurality of perspective images of the different angular projections of the targeted object 2, the slice images 32 generated by execution of the reconstructing process are a plurality of sectional views of the targeted object 2, the three-dimensional imaging data 34 may be displayed with a way of three-dimensional perspective model, so it is available for user to watch the three-dimensional imaging data 34 in different angular projections.

The present disclosed example can effectively generate the corresponding three-dimensional imaging data according to the imaging parameter set, and the generated three-dimensional imaging data has the maximum contrast-to-noise ratio. For example, if the user selects "rat" and 'bone", the bone (tested region) and muscle around the bone (reference region) of the generated three-dimensional imaging data have the maximum region difference (the region difference van be quantified via formula 1-3 described later).

Figure 4:
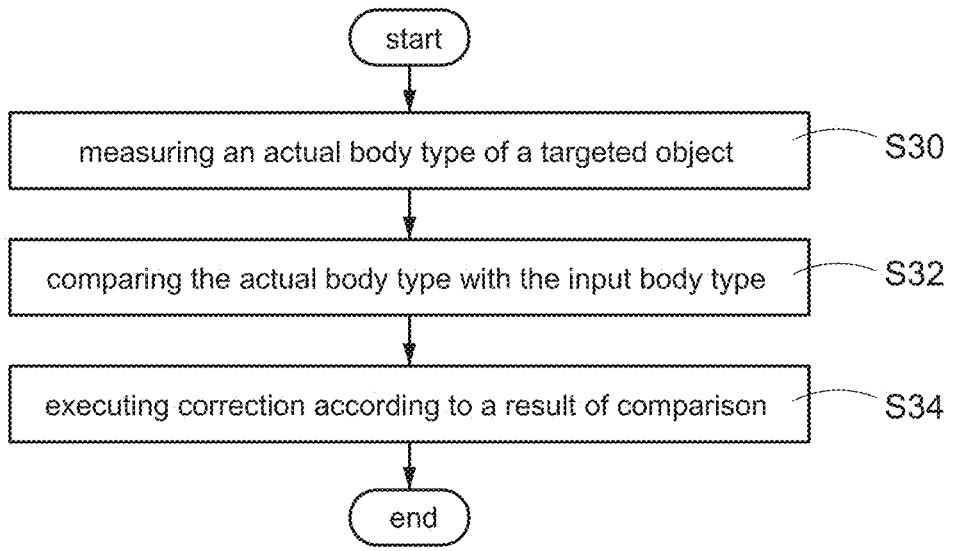
FIG. 4 is a flowchart of function of correcting body type according to one embodiment of the present disclosed example.

Please refer to FIG. 2 and FIG. 4. FIG. 4 is a flowchart of function of correcting body type according to one embodiment of the present disclosed example. The present disclosed example may further provide a function of detecting and correcting input body type. Via implement of the function of detecting and correcting input body type, the present disclosed example can detect whether the input body type is incorrect, and correct the incorrect input body type if the input body type is incorrect. More specifically, the imaging method of this embodiment comprises following steps being performed after the step S12 and before the step S16.

Step S30: the control module 100 measures an actual body type of the targeted object.

In one of the exemplary embodiments, the computed tomography system 1 comprises a distance-sensing device (such as infrared range finder, a laser range finder, or an ultrasonic range finder) electrically connected to control module 10. The control module 100 measures the actual body type of the targeted object via above-mentioned distance-sensing device.

In one of the exemplary embodiments, the control module 100 measures according to the input body type configured by the user. For example, if the input body style is "rat", the control module 100 measures whole body of the targeted object via the distance-sensing device, and configures the measurement result as the actual body type.

In one of the exemplary embodiments, the above-mentioned distance-sensing device is arranged on the electrical movable frame 110 or the bed 114, so as to measure the actual body type (such as area, length or width of the targeted object) of the targeted object accurately.

In one of the exemplary embodiments, the control module 100 retrieves an actual image of the targeted object (such as visible light image, thermal image, or two-dimensional X-ray image), and calculates the actual body type of the targeted object via execution of image process on the actual image described later.

Step S32: the control module 100 compares the measured actual body type with the input body type of the description data for obtaining a comparison result.

For example, if the actual body type matches with the input body type, the control module 100 may determine that the comparison result is "correct body type". If the actual body type doesn't match with the input body type, the control module 100 may determine that the comparison result is "incorrect body type".

In the other embodiment, if the actual is larger than the input body type, the control module 100 may determine that the comparison result is "body type too large". In the other embodiment, if the actual is smaller than the input body type, the control module 100 may determine that the comparison result is "body type too small".

Step S34: the control module 100 corrects the input body type of the description data according to the comparison result of the actual body type and the input body type.

In one of the exemplary embodiments, if the comparison result is "correct body type", the correction of the actual input may be omitted by the control module 100.

If the comparison result is "incorrect body type", the control module 100 may issue an alarm via the human-machine interface 108.

In one of the exemplary embodiments, the control module 100 may automatically correct the input body type of the description data if the comparison result of the actual body type and the input body type is "incorrect body type".

For example, if the comparison result is "actual body type too large", the control module 100 may directly increase the input body type by one level, such as modifying the "mouse" into "raft". If the comparison result is "actual body type too small", the control module 100 may directly reduce the input body type by one level, such as modifying the "raft" into "mouse".

The present disclosed example can effectively prevent the generated three-dimensional imaging data from incorrect via detecting automatically whether the body type inputted by the user is incorrect.

Figure 5:
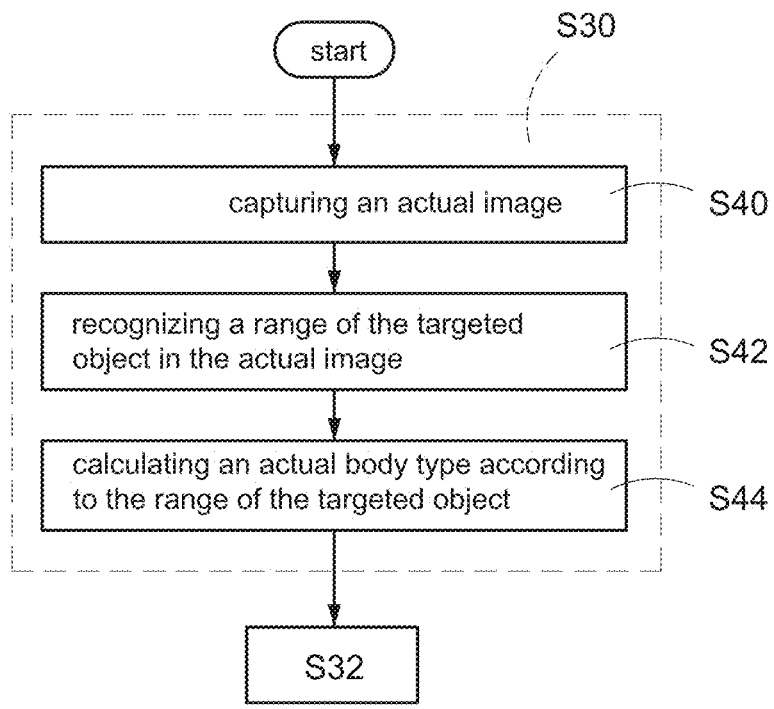
FIG. 5 is a partial flowchart of function of correcting body type according to one embodiment of the present disclosed example.

Please refer to FIG. 2, FIG. 4 and FIG. 5. FIG. 5 is a partial flowchart of function of correcting body type according to one embodiment of the present disclosed example. In this embodiment, the control module 100 calculates the actual body type of the targeted object according to the actual image of the targeted object. Compared with the embodiment shown in FIG. 4, the step S30 of this embodiment further comprises following steps.

Step S40: the control module 100 controls an image capture device to shoot the targeted object for obtaining the actual image (such as visible light image, thermal image, or two-dimensional X-ray image).

In one of the exemplary embodiments, if the actual image is visible light image or thermal image, the computed tomography system 1 may comprises an image capture device (such as visible light camera or thermal image camera) electrically connected to the control module 100. The above-mentioned image capture device is arranged corresponding to the bed 114 or on the bed 114. The control module 100 may control above-mentioned image capture device to shoot the targeted object for retrieving the actual image (such as visible light image or thermal image).

In one of the exemplary embodiments, the control module 100 may execute a pre-scanning (namely, a two-dimensional imaging operation) according to a default imaging parameter set or the selected imaging parameter set for obtaining the actual image (two-dimensional X-ray image).

Step S42: the control module 100 executes a process of recognizing object image on the actual image for recognizing a range of the targeted object in the actual image.

Step S44: the control module 100 calculates the actual body type of the targeted object according to the recognizing range of the targeted object.

The present disclosed example can effectively calculate the actual body type of the targeted object, so as to effectively correct the input body type.

Please note that although the present disclosed example corrects the input body type in the above-mentioned embodiment shown in FIG. 4 and FIG. 5, but this specific example is not intended to limit the scope of the present disclosed example. In the other embodiment, the embodiments shown in FIG. 4 and FIG. 5 may be modified to correct the input thickness.

Figure 6:
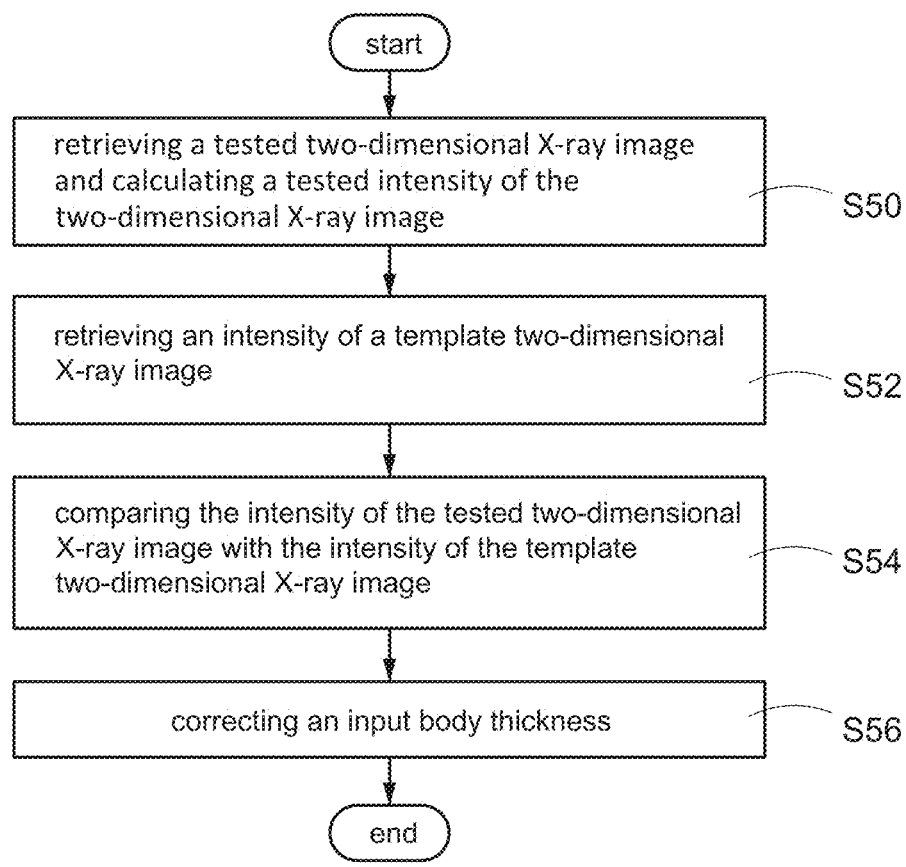
FIG. 6 is a flowchart of function of detecting body thickness according to one embodiment of the present disclosed example.

Please refer to FIG. 2 and FIG. 6. FIG. 6 is a flowchart of function of detecting body thickness according to one embodiment of the present disclosed example. The present disclosed example further provides a function of detecting and correcting body thickness. Via implement of the function of detecting and correcting body thickness, the present disclosed example may detect whether the actual body thickness of the targeted object matches with the input body thickness or not, and correct the input body thickness if actual body thickness and input body thickness don't match with each other. More specifically, the description data of this embodiment further comprises an input body thickness, each of the template data comprises a template body thickness.

In this embodiment, each of the input body type may be determined by the input body thickness, or be divided into a plurality of various body thickness ranges. The control module 100 may select the matched imaging parameter set according to the input body thickness inputted by the user.

For example, the body type "rat" may be divided into three body thickness selection, such as "thick body thickness" correspond to "larger than 7 centimeter", "normal body thickness" correspond to "5-7 centimeter", and "thin body thickness" correspond to "less than 5 centimeter". In another example, the body type "mouse" may be divided into three body thickness selection, such as "thick body thickness" correspond to "larger than 5 centimeter", "normal body thickness" correspond to "3-5 centimeter", and "thin body thickness" correspond to "less than 3 centimeter".

The imaging method of this embodiment further comprises following steps used to implement the function of detecting and correcting body thickness which are performed between the step S12 and S16.

Step S50: before execution of the two-dimensional imaging operation, the control module 100 controls the X-ray tube 102, the filter module 104 and the image detector 106 to execute the two-dimensional imaging operation on the targeted object placing on the bed 114 according to the default imaging parameter set or the selected imaging parameter set for obtaining a tested two-dimensional imaging image (tested two-dimensional X-ray image). Then, the control module 100 calculates an intensity of the two-dimensional X-ray image.

Please note that, steps S50-S56 of the imaging method of this embodiment is configured to be performed after the step S14 if the control module 100 is configured to execute two-dimensional imaging operation according to the selected imaging parameter set.

In one of the exemplary embodiments, the control module 100 is configured to control the computed tomography system 1 to execute the two-dimensional imaging operation on the front or side of the targeted object for obtaining the tested two-dimensional X-ray image of the front or side of the targeted object.

In one of the exemplary embodiments, the control module 100 calculates an average image intensity (such as the average of all of the pixel values) of the tested two-dimensional X-ray image, weighted image intensity (such as the weighted average of all of the pixel values) or local image intensity (such as the average of the pixel values in the central region or other designated region).

Step S52: the control module 100 retrieves an image intensity of a template two-dimensional imaging image (template two-dimensional X-ray image) corresponding to the description data.

One of the exemplary embodiments, the memory module 112 stored a plurality of template two-dimensional X-ray images in advance, the template two-dimensional X-ray images respectively correspond to the various template body thickness (such as each template two-dimensional X-ray image is obtained by execution of two-dimensional imaging operation on the targeted object having the different body thicknesses respectively in advance).

More specifically, the control module 100 first load a template two-dimensional X-ray image form the memory module 112, the template body thickness corresponding to the loaded template two-dimensional X-ray image matches the input body thickness. Then, the control module 100 calculates the image intensity (such as pixel values) of the loaded two-dimensional X-ray image, such as average image intensity (such as the average of all pixel values) of the tested two-dimensional X-ray image, weighted image intensity (such as the weighted average of all of the pixel values) or local image intensity (such as the average of the pixel values in the central region or other designated region).

In the other embodiment, the memory module 112 stores the image intensities of each two-dimensional X-ray image, so as to omit above-mentioned calculation of image intensity and improve process performance.

Step S54: the control module 100 compares the image intensity of the tested two-dimensional X-ray image with the image intensity of the template two-dimensional X-ray image for obtaining the comparison result.

In one of the exemplary embodiments, if the image intensity of the template two-dimensional X-ray image is consistent with the image intensity of the template two-dimensional X-ray image (such as a difference between the image intensity of the template two-dimensional X-ray image and the image intensity of the template two-dimensional X-ray image is not larger than a default value), the control module 100 may determine that the comparison result is "correct body thickness". If the image intensity of the template two-dimensional X-ray image is not consistent with the image intensity of the template two-dimensional X-ray image (such as a difference between the image intensity of the template two-dimensional X-ray image and the image intensity of the template two-dimensional X-ray image is larger than a default value), the control module 100 may determine that the comparison result is "incorrect body thickness".

In one of the exemplary embodiments, if the image intensity of the template two-dimensional X-ray image is less than the image intensity of the template two-dimensional X-ray image (namely, the actual thickness of the targeted object is larger than the template thickness corresponding to the template two-dimensional X-ray image), the control module 100 may determine that the comparison result is "the targeted object is too thick". If the image intensity of the template two-dimensional X-ray image is larger than the image intensity of the template two-dimensional X-ray image (namely, the actual thickness of the targeted object is less than the template thickness corresponding to the template two-dimensional X-ray image), the control module 100 may determine that the comparison result is "the targeted object is too thin".

Step S56: the control module 100 corrects the input body thickness of the description data according to the comparison result.

In one of the exemplary embodiments, if the comparison result is "correct body thickness", the control module 100 doesn't correct the input thickness of the description data. If the comparison result is "incorrect body thickness", the control module 100 corrects the input thickness of the description data.

In one of the exemplary embodiments, if the comparison result is "incorrect body thickness", the control module 100 may continue to retrieve the image intensities of the other template two-dimensional X-ray images, and compares the image intensity of the tested two-dimensional X-ray image with the retrieved image intensities of the other template two-dimensional X-ray images one by one. Then, the control module 100 configures the template body thickness corresponding to the template two-dimensional X-ray image having the consistent image intensity as the new input body thickness for completing the correction.

In one of the exemplary embodiments, if the comparison result is "the targeted object is too thick", the control module 100 may directly increase the input body thickness by one level, such as modifying the "normal body thickness" into "thick body thickness". If the comparison result is "the targeted object is too thin", the control module 100 may directly reduce the input body thickness by one level, such as modifying the "normal body thickness" into "thin body thickness".

In one of the exemplary embodiments, if the comparison result is "incorrect body thickness", the control module 100 may issue an alarm via the human-machine interface 108 for indicating the user to input the correct body thickness.

Via detecting the body thickness automatically, the present disclosed example can effectively prevent the quality of the generated three-dimensional imaging data form poor caused by error of body thickness.

Figure 7:
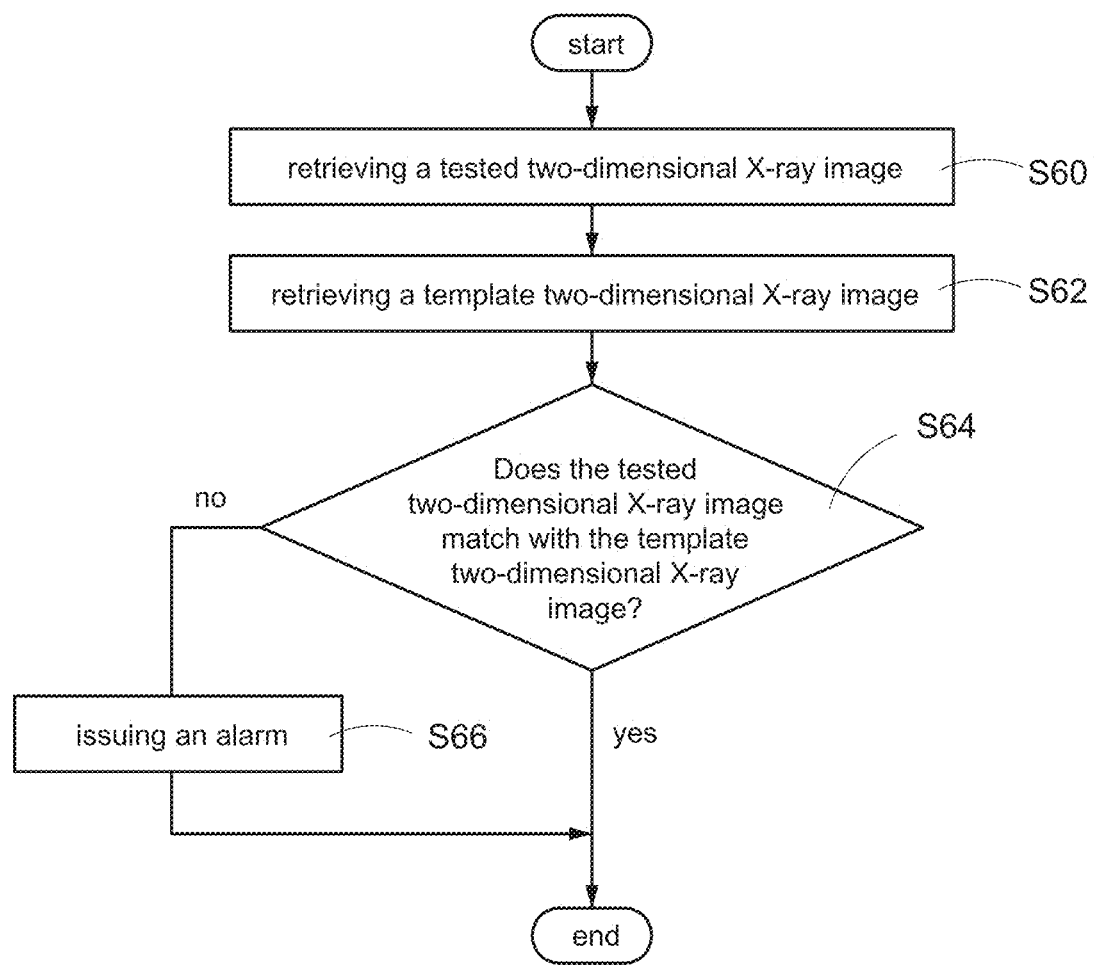
FIG. 7 is a flowchart of function of detecting application according to one embodiment of the present disclosed example.

Please refer to FIG. 2 and FIG. 7. FIG. 7 is a flowchart of function of detecting application according to one embodiment of the present disclosed example. The present disclosed example may further provide a function of detecting application. Via implement the function of detecting application, the present disclosed example may detect whether the input application of the description data is incorrect. More specifically, the imaging method of this embodiment may further comprise following steps which is configured to be performed after step S12 and before step S16.

Step S60: the control module 100 controls the computed tomography system 1 to execute a pre-scanning (namely, the two-dimensional imaging operation) for obtaining the tested two-dimensional X-ray image according to the default imaging parameter set or the selected imaging parameter set.

Please note that steps S60-S66 of the imaging method of this embodiment are configured to be performed after step S14 if the control module 100 is configured to execute two-dimensional imaging operation according to the selected imaging parameter set.

Step S62: the control module 100 retrieves the template two-dimensional X-ray image corresponding to the description data. More specifically, the memory module 112 stored a plurality of template two-dimensional X-ray images in advance, the plurality of the template two-dimensional X-ray images correspond to a plurality of the various template application. The template application corresponding to the loaded template two-dimensional X-ray image matches with the input application.

Step S64: the control module 100 compares the tested two-dimensional X-ray image with the template two-dimensional X-ray image for recognizing whether the tested two-dimensional X-ray image is consistent with the template two-dimensional X-ray image, and retrieves the recognition result. If both are consistent with each other, the control module 100 determines that the description data is correct, configures the recognition result as "matched", and terminate the application detection. If both are not consistent with each other, the control module 100 determines that the description data is incorrect, configures the recognition result as "failure of recognition", and performs the step S66.

Step S66: the control module 100 issues an alarm message via the human-machine interface 108 for indicating the user to re-check whether the inputted description data is correct or not. The present disclosed example can effectively prevent the quality of the three-dimensional imaging data from poor via automatically detecting whether the input application is correct or not.

Please note that, in the embodiment shown in FIG. 6 or the embodiment shown in FIG. 7, the control module 100 can first execute following operations to generate a plurality of template two-dimensional X-ray images before switching to the intelligent imaging mode.

The control module 100 controls the computed tomography system 1 to execute two-dimensional imaging operations many times for obtaining a plurality of two-dimensional X-ray images (namely, the sample two-dimensional X-ray images) according to each of 3D imaging requirements (such as each of the targeted objects respectively having the various body thickness, or each of applications of the same targeted object).

For example, the control module 100 may execute the two-dimensional imaging operations many times on the rat according to the various imaging parameter sets for obtaining a plurality of sample two-dimensional X-ray image of the rat, execute the two-dimensional imaging operations many times on the small dog according to the various imaging parameter sets for obtaining a plurality of sample two-dimensional X-ray image of the small dog, or execute the two-dimensional imaging operations on the small dogs respectively having various body thicknesses according to the various imaging parameter sets for obtaining a plurality of sample two-dimensional X-ray image of the small dogs respectively having various body thicknesses.

Then, the control module 100 executes an image process on the plurality of the obtained sample two-dimensional X-ray image for obtaining a template two-dimensional X-ray image.

In one of the exemplary embodiments, the control module 100 executes image alignment process on the plurality of the sample two-dimensional X-ray images for aligning the sample two-dimensional X-ray images, executes image smoothing process on the sample two-dimensional X-ray images for filtering out a high-frequency part (the detail of image) of the sample two-dimensional X-ray images for making the sample two-dimensional X-ray images be similar as each other, and executes an image merging process on the sample two-dimensional X-ray images for obtaining a template two-dimensional X-ray image.

In one of the exemplary embodiments, above-mentioned image merging process is an image average processing, the control module 100 is configured to execute an average calculation on the pixel values of the pixels located at the same position of the sample two-dimensional X-ray image, and configures the calculated pixel value as the pixel values of the pixels located at the same position of the template two-dimensional X-ray image.

Thus, the present disclosed example can effectively generate the template two-dimensional X-ray image corresponding to the various three-dimensional imaging requirement.

Figure 8:
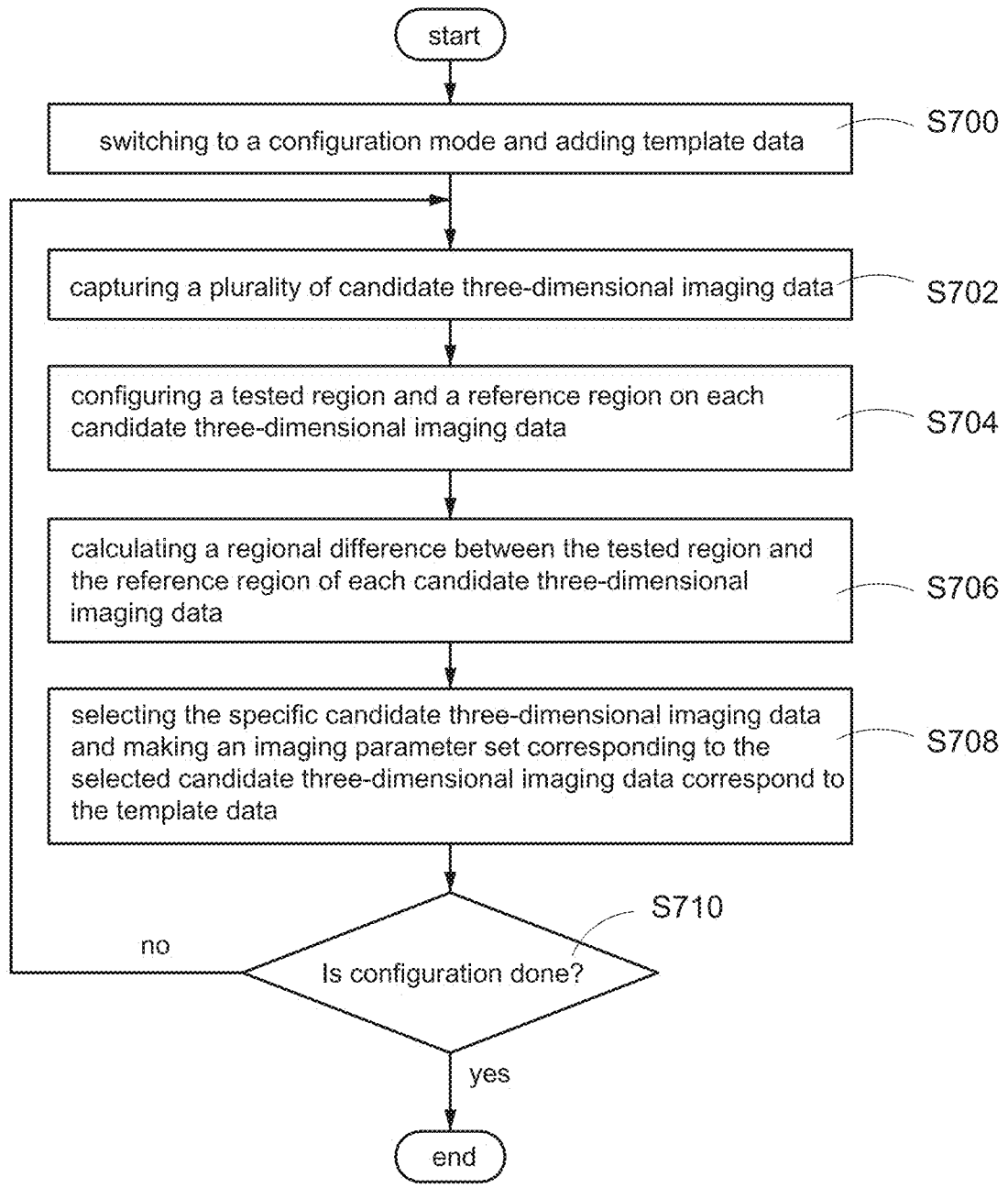
FIG. 8 is a flowchart of configuration of template data according to one embodiment of the present disclosed example.

Please refer to FIG. 2 and FIG. 8. FIG. 8 is a flowchart of configuration of template data according to one embodiment of the present disclosed example. The present disclosed example further provides a function of configuration of template data. Via implement of the function of configuration of template data, the present disclosed example can make the user be convenient to configure the new template data. The imaging method of this embodiment further comprises following steps for implement of the function of configuration of template data.

Step S700: the control module 100 switches to a configuration mode. More specifically, the control module 100 switches to the configuration mode after a default condition satisfies (such as receiving an operation of switching to configuration mode from the user via the human-machine interface 108).

In the configuration mode, the user may operate the human-machine interface 108 to add one template data (such as inputting a new template body type, a new template application and/or a new template body thickness).

Then, the user may place the targeted object (template object) corresponding to the added template data on the bed 114.

For example, if the template data is {big dog, bone}, the user may place a big dog or the corresponding prosthesis (prosthesis may be an acrylic prosthesis having a cavity, a material having the density being similar as the bone is filled with the cavity) on the bed 114.

Step S702: the control module 100 controls the computed tomography system 1 to execute three-dimensional imaging operation many times according to the various imaging parameter sets for obtaining a plurality of three-dimensional imaging data.

In one of the exemplary embodiments, each of imaging parameter sets may comprise each of various X-ray tube voltages, each of the various filter parameters, and each of the various projection numbers.

Step S704: the control module 100 executes a partition process (according to the user's operation) to configure a tested region (such as the region of bone) and a reference region (such as the region adjacent the bone) on each of a plurality of candidate three-dimensional imaging data.

Step S706: the control module 100 calculates a regional difference between the tested region and the reference region of each candidate three-dimensional imaging data.

Step S708: the control module 100 selects the specific candidate three-dimensional imaging data and makes an imaging parameter set corresponding to the selected candidate three-dimensional imaging data correspond to the template data.

In one of the exemplary embodiments, the control module 100 selects the candidate three-dimensional imaging data having the highest regional difference (namely, the difference between the tested region and the reference region of the selected candidate three-dimensional imaging data is most obvious), and makes the imaging parameter set corresponding to the selected candidate three-dimensional imaging data correspond to the template data added in step S700.

Step S710: the control module 100 determines whether any template data is necessary to be configured.

If the control module 100 determines that the configuration is not done (such as any template data is necessary to be configured), the control module 100 adds another template data (such as {rat, kidney}), and performs steps S702-S708 for make the added template data correspond to another imaging parameter set. Otherwise, the control module 100 determines that all of the configurations are done, and leaves the configuration mode.

Figure 9:
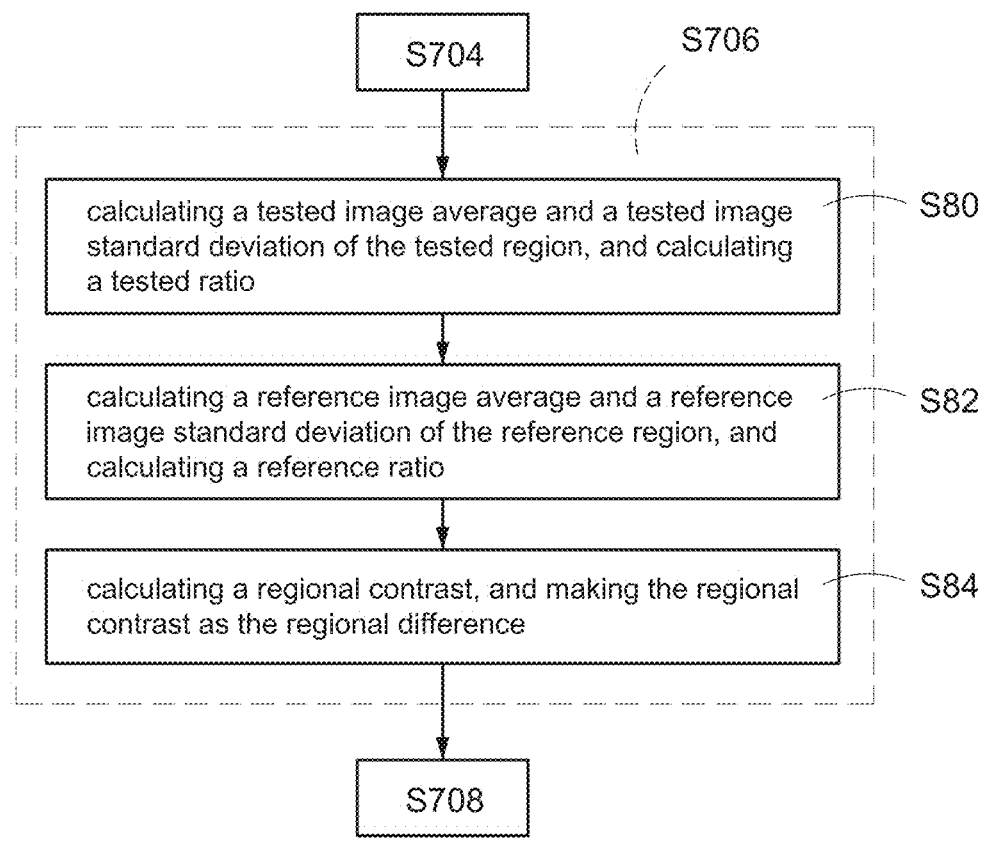
FIG. 9 is a flowchart of calculation of regional difference according to one embodiment of the present disclosed example.

Please refer to FIG. 2, FIG. 8 and FIG. 9. FIG. 9 is a flowchart of calculation of regional difference according to one embodiment of the present disclosed example. Compare to the embodiment shown in FIG. 8, the step S706 of this embodiment comprises follow steps.

Step S80: the control module 100 calculates a tested image average (such as an average of all of the pixel values in the tested region) and a tested image standard deviation (such as a standard deviation of all of the pixel values in the tested region) of the tested region, and calculating a tested ratio of the tested image average to the tested image standard deviation.

In one of the exemplary embodiments, the control module 100 calculates the tested ratio via following formula 1.

$$R_A = \frac{\mu_A}{\sigma_A} \quad \text{formula 1}$$

wherein, $R_A$ is the tested ratio, $\mu_A$ is the tested image average, and $\sigma_A$ is the tested image standard deviation.

Step S82: the control module 100 calculates a reference image average (such as an average of all pixel values in the reference region) and a reference image standard deviation (such as a standard deviation of all of the pixel values in the reference region) of the reference region, and calculating a reference ratio of the reference image average to the reference image standard deviation.

In one of the exemplary embodiments, the control module 100 calculates the reference ratio via following formula 2.

$$R_B = \frac{\mu_B}{\sigma_B} \quad \text{formula 2}$$

wherein, $R_B$ is the reference ratio, $\mu_B$ is the reference image average, and $\sigma_B$ is the reference image standard deviation.

Step S84: the control module 100 calculates a difference between the between the tested ratio and the reference ratio, and configures the calculated difference as the regional difference.

In one of the exemplary embodiments, the control module 100 calculates the regional contrast via following formula 3.

$$C = |R_A - R_B| \quad \text{formula 3}$$

wherein C is the regional contrast, $R_A$ is the tested ratio, and $R_B$ is the reference ratio.

The present disclosed example can determine a difference level between the different regions in the image according to the regional contrast, effectively quantify the difference, and effectively determine the candidate three-dimensional imaging data having the most obvious regional difference (namely, the candidate three-dimensional imaging data has the best contrast-to-noise ratio).

What is claimed is:

1. An imaging method for a computed tomographic system, the imaging method comprising the steps of:
    a) controlling a computed tomographic system to receive a description operation for configuring description data under an intelligent imaging mode;
    b) selecting one of pre-stored two-dimensional X-ray images according to the description data, and displaying the selected pre-stored two-dimensional X-ray image, wherein the pre-stored two-dimensional X-ray images are pre-stored in a memory module and respectively correspond to a plurality of different template data, and the template data corresponding to the pre-stored two-dimensional X-ray image being selected is consistent with the description data;
    c) after the step b), selecting one of a plurality of imaging parameter sets corresponding to one of the plurality of different template data, wherein the template data corresponding to the selected imaging parameter set is consistent with the description data, each of the imaging parameter sets is configured to maximize a contrast-to-noise ratio of the three-dimensional imaging data being consistent with the corresponding template data, each of the imaging parameter sets comprises at least two of a X-ray tube voltage, a filter parameter, and a projection number; and
    d) controlling an X-ray tube, a filter module or an image detector of the computed tomographic system to execute a three-dimensional imaging operation according to the selected imaging parameter set for obtaining the three-dimensional imaging data being consistent with the description data.

2. The imaging method according to claim 1, wherein the template data comprises a template application and a template body type, and the step a) comprises the steps of:
    a1) displaying a plurality of application options and a plurality of options of body type under the intelligent imaging mode;
    a2) receiving the description operation for selecting one of the application options and one of the body type options; and
    a3) configuring an input application of the description data according to the selected application option, and configuring an input body type of the description data according to the selected body type option;
    wherein the step c) is configured to recognize the template data comprising the template application matching with the input application and the template body type matching with input body type, and select the imaging parameter set corresponding to the template data.

3. The imaging method according to claim 1, further comprising, after the step c) and before the step d), the steps of:
- c1) executing a two-dimensional imaging operation for obtaining a tested two-dimensional X-ray image according to the selected imaging parameter set, and displaying the tested two-dimensional X-ray image; and
- c2) receiving an adjustment operation, and adjusting the imaging parameter set according to the adjustment operation;
- wherein the step d) is configured to control the computed tomography system to execute the three-dimensional imaging operation according to the adjusted imaging parameter set.

4. The imaging method according to claim 1, wherein the step d) comprises the steps of:
- d1) controlling the X-ray tube, the filter module, the image detector, and an electrical movable frame to execute a two-dimensional imaging operation for obtaining a plurality of two-dimensional X-ray images respectively corresponding to different angular projections according to the X-ray tube voltage, the filter parameter, the projection number, an exposure time, and an effective focal spot size of the selected imaging parameter set;
- d2) executing a reconstructing process in the two-dimensional X-ray images for obtaining a plurality of slice images; and
- d3) executing a three-dimension image display on the slice images for obtaining the three-dimensional imaging data.

5. The imaging method according to claim 1, further comprising, after the step a) and before the step d), the steps of:
- f1) measuring an actual body type of the targeted object; and
- f2) issuing an alarm or correcting an input body type of the description data if the actual body type doesn't match with the input body type of the description data.

6. The imaging method according to claim 5, wherein the step f1) comprises the steps of:
- f11) capturing the targeted object for obtaining an actual image;
- f12) recognizing a range of the targeted object in the actual image; and
- f13) calculating the actual body type of the targeted object according to the range of the targeted object.

7. The imaging method according to claim 5, wherein the step f1) is configured to measure the actual body type of the targeted object via an infrared range finder, a laser range finder, or an ultrasonic range finder.

8. The imaging method according to claim 1, further comprising, after the step a) and before the step d), the steps of:
- g1) executing a two-dimensional imaging operation on the targeted object for obtaining a tested two-dimensional X-ray image and calculating an intensity of tested two-dimensional X-ray image;
- g2) selecting one of a plurality of template two-dimensional X-ray images according to an input body thickness of the description data, and retrieving an intensity of the template two-dimensional X-ray image; and
- g3) correcting the input body thickness of the description data if the intensity of the tested two-dimensional X-ray image doesn't match with an intensity of the template two-dimensional X-ray image.

9. The imaging method according to claim 1, further comprising, after the step a) and before the step d), the steps of:
- h1) executing a two-dimensional imaging operation on the targeted object for obtaining a tested two-dimensional X-ray image;
- h2) selecting one of a plurality of template two-dimensional X-ray images according to an input application of the description data; and
- h3) issuing an alarm if determining that the tested two-dimensional X-ray image doesn't match with the template two-dimensional X-ray image.

10. The imaging method according to claim 1, further comprising the steps of:
- i1) adding the template data at a configuration mode;
- i2) executing a three-dimensional imaging operation more than one times on the targeted object for obtaining a plurality of candidate three-dimensional imaging data according to the imaging parameter sets, wherein the targeted object matches with the added template data;
- i3) configuring a tested region and a reference region of each of the plurality of the candidate three-dimensional imaging data;
- i4) calculating a regional difference between the tested region and the reference region of each of the plurality of the candidate three-dimensional imaging data; and
- i5) making the imaging parameter set correspond to the template data, wherein the imaging parameter set corresponding to the candidate three-dimensional imaging data having a highest regional difference.

11. The imaging method according to claim 10, wherein the step i2) is configured to executing the three-dimensional imaging operation more than one time according to at least two of the different X-ray tube voltages, the filter parameter, and the projection number.

12. The imaging method according to claim 11, wherein the step i4) comprises the steps of:
- i41) calculating a tested image average and a tested image standard deviation of the tested region of each of the plurality of the candidate three-dimensional imaging data, and calculating a tested ratio of the tested image average to the tested image standard deviation;
- i42) calculating a reference image average and a reference image standard deviation of the reference region of each of the plurality of the candidate three-dimensional imaging data, and calculating a reference ratio of the reference image average to the reference image standard deviation; and
- i43) calculating a difference between the tested ratio and the reference ratio as the regional difference.

* * * * *